United States Patent [19]

Roevens et al.

[11] 3,991,072

[45] Nov. 9, 1976

[54] RACEMIZATION OF LOWER ALKYL IMIDAZOLE CARBOXYLATES

[75] Inventors: Leopold Fr. C. Roevens, Rijkevorsel; Jozef J. P. Heykants, Vosselaar; Walter A. M. Helsen, Wilrijk, all of Belgium

[73] Assignee: Janssen Pharmaceutica N.V., Beerse, Belgium

[22] Filed: Sept. 12, 1975

[21] Appl. No.: 612,830

Related U.S. Application Data

[62] Division of Ser. No. 557,194, March 10, 1975.

[52] U.S. Cl. ................................ 260/309; 260/999
[51] Int. Cl.² ...................................... C07D 233/90
[58] Field of Search ...................................... 260/309

[56] References Cited

OTHER PUBLICATIONS

Fieser et al., Advanced Organic Chemistry, pp. 89–90, N.Y., Reinhold, 1961.

Hofmann, Imidazole and its Derivatives, Part I, p. 201, N.Y., Interscience, 1953.

*Primary Examiner*—Natalie Trousof
*Attorney, Agent, or Firm*—Salvatore R. Conte

[57] ABSTRACT

Novel methods of preparing lower alkyl 1-(1-phenylethyl)-1H-imidazole-5-carboxylates in racemic as well as in optically pure isomeric form.

4 Claims, No Drawings

RACEMIZATION OF LOWER ALKYL IMIDAZOLE CARBOXYLATES

CROSS-REFERENCE TO RELATED APPLICATION

This is a divisional application of my copending application Ser. No. 557,194, filed Mar. 10, 1975.

DESCRIPTION OF THE INVENTION

The imidazole carboxylates with which this invention is concerned are generally represented by the formula:

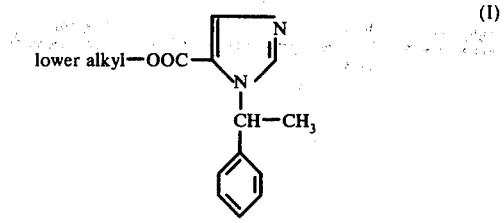

and the stereochemical optical isomers thereof, wherein the term "loweralkyl" is selected from the group consisting of methyl, ethyl and propyl. The pharmaceutically acceptable acid addition salts thereof are meant to be within the scope of formula (I).

Compounds of formula (I) in racemic form and methods of preparing same are described in U.S. Pat. No. 3,354,173.

The compounds of formula (I), and especially the dextrorotatory isomers thereof, having the R-configuration, are very useful as short-acting hypnotic agents, and some of them are now currently used in practice or well-known in the art. Important members of the group of compounds within the scope of formula (I) are, for example, ($\pm$)-methyl 1-(1-phenylethyl)imidazole-5-carboxylate, generically designated as metomidate, which is commercially available in Europe as an injectable hypnotic for veterinary use; R-(+)-ethyl 1-(1-phenylethyl)-1H-imidazole-5-carboxylate, generically designated as etomidate, reports of which have appeared in Arzneim.-Forsch., 21 (8), 1234 (1971), Brit. J. Anaesthesia, 45, 1097 (1973), and Anaesthesist, 23, 150 (1974); and ($\pm$)-propyl 1-(1-phenylethyl)-1H-imidazole-5-carboxylate, generically designated as propoxate.

According to this invention, the compounds of formula (I) are conveniently obtained by transforming 1-(1-phenylethyl)-1H-imidazole-5-carboxamide or 1-(1-phenylethyl)-1H-imidazole-5-carbonitrile into a loweralkyl ester of formula (I), such as, for example, by heating, preferably under reflux conditions, 1-(1-phenylethyl)-1H-imidazole-5-carboxamide (II) or 1-(1-phenylethyl)-1-H-imidazole-5-carbonitrile (III) together with an appropriate lower alkanol in the presence of a suitable acid, preferably a strong mineral acid, such as, for example, hydrochloric or sulfuric acid. The thus-obtained compounds of formula (I) may be isolated from the reaction mixture and further purified by classical means and, if desired, transformed into a pharmaceutically acceptable acid addition salt thereof by reacting them with an appropriate acid.

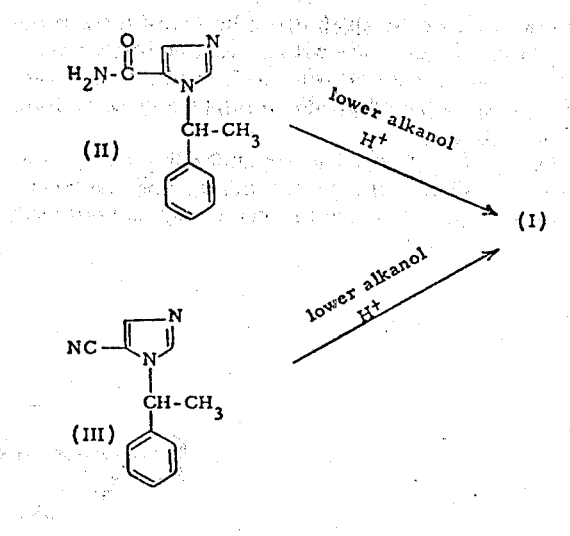

Since the stereochemical configuration at the asymmetric carbon atom in either (II) or (III) is not altered during the course of the reaction, the foregoing procedure may be employed to prepare the racemic form of the compounds (I) as well as the optically pure isomeric forms thereof having either the R-(+) or S-(−) configuration, provided that the corresponding form of the precursors (II) or (III) is used as a starting material.

The 1-(1-phenylethyl)-1H-imidazole-5-carboxamide (II) and the 1-(1-phenylethyl)-1H-imidazole-5-carbonitrile (III) used herein as starting materials may be prepared by the following sequence of reactions.

N-(1-phenylethyl)-aminoacetonitrile (IV) is N-acylated in the conventional manner with a lower aliphatic acylating agent for example, with formic acid or with an appropriate lower alkanoic acid anhydride or halide, preferably the chloride, such as, for example, acetic anhydride, acetyl chloride, propionic anhydride, and the like, to produce the corresponding N-acylaminoacetonitrile (V). The N-acylated aminoacetonitrile is then C-formylated using a lower alkyl ester of formic acid, e.g. methyl formate, with an alkali alkoxide, e.g. sodium methoxide, in an inert solvent such as, for example, an aromatic hydrocarbon, e.g., benzene, toluene, xylene and the like, an ether, e.g. tetrahydrofuran, dioxane and the like, and other aprotic organic solvents.

The resulting alkali metal enolate salt (VI) can be isolated by adding several volumes of ether and filtering off the solid salt. Alternatively the alkali metal enolate salt need not be isolated but may be extracted with water and the aqueous solution as such employed thereafter.

The free N-acyl-C-formylaminoacetonitrile enol (VII) can be obtained by acidifying an aqueous solution of the corresponding salt (VI). Isolation of the free enol (VII) may be effected with a water-immiscible solvent such as chloroform.

The enol (VII) is then subjected to a condensation reaction with hydrogen thiocyanate in an aqueous solution using approximately equivalent molecular quantities of the reactants to obtain 2-mercapto-1-(1-phenylethyl)-1H-imidazole-5-carboxamide (VIII). Alternatively, condensation may be accomplished with water-soluble metal salts, preferably the alkali metal salts such as sodium and potassium salts of one or both of the reactants, in which case the reaction is carried out in the presence of a strong, non-oxidizing mineral acid, such as hydrochloric acid, hydrobromic acid, phosphoric acid and the like to produce the acid form of the reactants.

The condensation solvent is preferably an aqueous solvent, such as, water or aqueous alcohol, containing sufficient water to retain in solution any inorganic salt which may be formed during the course of the reaction. Although room temperatures (20°–25° C.) are operable, slightly elevated temperatures of about 40°–100° C. will enhance the rate of the reaction. It is to be noted that during the foregoing condensation reaction, which occurs in acidic medium, the nitrile group of (VII) is hydrolyzed to a carboxamide group.

The desired 1-(1-phenylethyl)-1H-imidazole-5-carboxamide of formula (II) is then obtained by treating the amide of formula (VIII) with Raney-Nickel. The reaction is preferably carried out in a lower alkanol, e.g. ethanol, to which there is added an appropriate base, such as, for example, ammonia, to solubilize the reactant (VIII).

The 1-(1-phenylethyl)-1H-imidazole-5-carbonitrile of formula (III) is conveniently prepared by dehydration of the amide (II), e.g. with an amide-to-nitrile dehydrating agent such as, for example, phosphoryl chloride, phosphorus pentoxide, thionyl chloride and the like in an appropriate solvent, such as, for example, pyridine.

The foregoing reactions may be illustrated by the following schematic representation, wherein $R^1$ stands for hydrogen or loweralkyl.

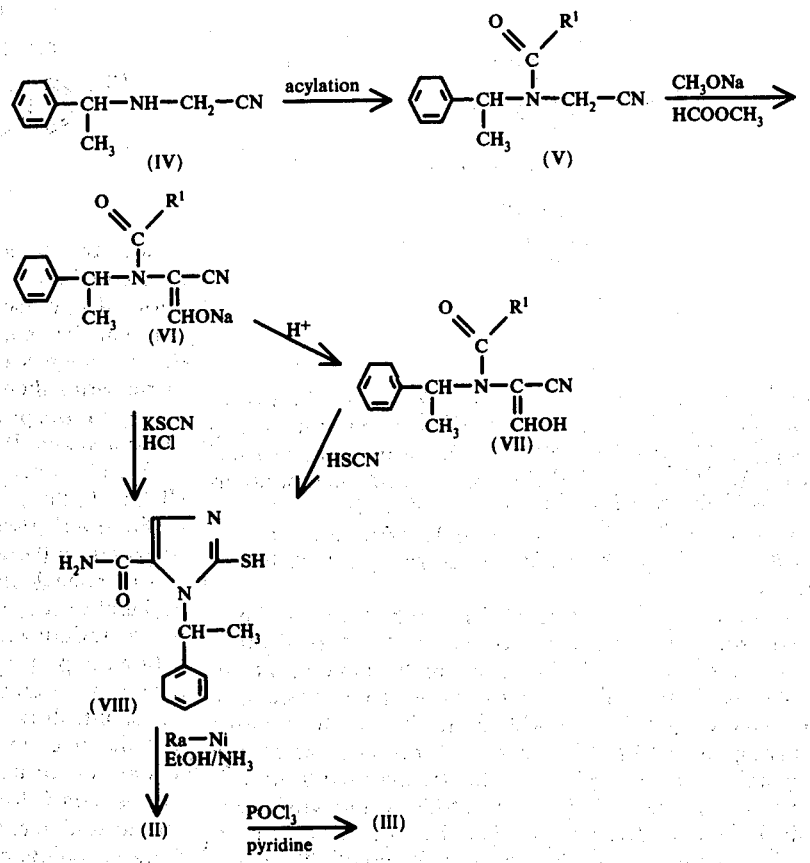

It is to be noted that when the precursor (IV), used as a starting material, is in the racemic form, then the resulting amide (II) and nitrile (III) are also in the racemic form. When (IV) has either the R- or S-configuration, substantially free of the other, the corresponding forms of (II) and (III) will respectively be obtained. The precursor of formula (IV) in racemic form as well as the optically pure isomers thereof are described in J. Org. Chem., 37 (21), 3286–3289 (1972).

The amide of formula (II) and the nitrile of formula (III), in racemic form and in the form of their optical isomers each substantially free of the other, are deemed to be novel, and, as useful precursors in the preparation of compounds of formula (I), they constitute an additional feature of this invention.

By the present invention there is also provided a method of preparing substantially pure optical antipodes of formula (I) essentially free of the other starting from racemic precursors. It is a highly desirable objective to have such a method available since it makes the production of optically pure end products to a lesser degree dependent on the availability of optically pure precursors.

A convenient method of preparing substantially pure R- and S-forms of formula (I) compounds according to the present invention comprises resolving racemic 1-(1-phenylethyl)-1H-imidazole-5-carboxylic acid into its optically active enantiomorphs and thereafter converting each optical isomer of the acid into the desired loweralkyl ester according to known esterification procedures.

The resolution of racemic 1-(1-phenylethyl)-1H-imidazole-5-carboxylic acid into its optical isomers may be carried out by salt formation with the appropriate isomeric form of a suitable optically active base, mechanically separating the insoluble diastereomeric salt thus formed, and liberating the corresponding free acid in the usual manner, for example, by treatment of the acid-base salt with suitable acid, e.g., a strong non-oxidizing mineral acid, in an amount sufficient to neutralize the basic moiety. If the imidazolecarboxylic acid is to be isolated it is appropriate to liberate first the free optically active base from the diastereomeric salt by the addition of aqueous alkali to about pH 11, thereafter extracting said base with an appropriate water-immiscible organic solvent such as, for example, 2,2'-oxybispropane, and adjusting the pH of remaining alkaline aqueous phase to neutral or slightly acidic with an appropriate acid, preferably a loweralkyl carboxylic acid such as, for example, acetic acid, propionic acid and the like, whereupon the desired imidazole-carboxylic acid precipitates. The optically active base used in the resolution is thereby recovered and, consequently, the need for additional optically pure reagents is minimalized.

The formation of the aforementioned diastereomeric salts is conducted in an appropriate inert organic solvent such as, for example, a lower alkanol, e.g. ethanol, propanol, 2-propanol, and the like, preferably under reflux conditions. Suitable optically active bases for the purpose of this invention, include, for example, the dextro- and levo-forms of (1-phenylethylamine, 1-(1-naphthyl)ethylamine, and 1-(2-naphthyl)ethylamine, the first being preferred.

For example, when R-(+)-1-phenylethylamine is added to a solution of racemic 1-(1-phenylethyl)-1H-imidazole-5-carboxylic acid in an appropriate solvent, an addition salt of R-(+)-1-(1-phenylethyl)-1H-imidazole-5-carboxylic acid with R-(+)-1-phenylethylamine in substantially pure form is precipitated, from which the free acid may be obtained in essentially optically pure form.

The thus-obtained R-(+)-1-(1-phenylethyl)-1H-imidazole-5-carboxylic acid or the addition salt thereof with R-(+)-1-phenylethylamine is easily converted into a R-(+)-loweralkyl 1-(1-phenylethyl)-1H-imidazole-5-carboxylate, designated as R-(+) (I), according to conventional esterification methods, for example, by refluxing the acid or the addition salt in an appropriate lower alkanol in the presence of an appropriate strong non-oxidizing mineral acid such as, for example, hydrochloric or sulfuric acid. Alternatively, the R-(+) acid may be transformed into an acyl halide according to standard procedures and the acyl halide reacted with an appropriate lower alkanol to obtain the desired ester. For example, the hydroxy function of the acid can be readily transformed into a chloro function by reaction of the acid with such chloro-transfer agents as oxalyl chloride, sulfinyl chloride (thionyl chloride) which is preferred, sulfuryl chloride, phosphorus oxychloride, phosphorus trichloride and phosphorus pentachloride. The thus-obtained R-(+) (I) product may be further purified by known purification procedures and, if desired, transformed into a pharmaceutically acceptable acid addition salt thereof by reacting it with an appropriate acid.

The same procedure may be utilized equally well, mutatis mutandis, to separate S-(−) 1-(1-phenylethyl)-1H-imidazole-5-carboxylic acid, using, however, the alternate S-(−) isomeric form of the optically active base. Similarly, esterification of the thus-obtained S-(−) acid yields the S-(−) form of the formula (I) esters, designated as S-(−) (I).

Whether the R-(+) or S-(−) form of the carboxylic acid is removed from the medium in diastereomeric salt form, the respective enantiomer which remains in the solution may be recovered by conventional means for example, by evaporation of the mother liquor from which the precipitated diastereomer was obtained or by dilution with an appropriate non-solubilizing solvent, and, if desired, transformed into a lower akyl ester of formula (I), having the corresponding configuration.

The racemic 1-(1-phenylethyl)-1H-imidazole-5-carboxylic acid used as a starting material herein is described in U.S. Pat. No. 3,354,173 and may be prepared according to the procedures outlined therein.

It is believed that the substantially pure optically isomeric forms of 1-(1-phenylethyl)-1H-imidazole-5-carboxylic acid and addition salts thereof with optically active bases, essentially free of their other respective enantiomers are novel and, as useful intermediates herein, they constitute an additional feature of this invention. In addition to salt formation with bases, the dextro- and levo-forms of the imidazole-carboxylic acids may also form acid addition salts with acids.

In view of the basic properties of the imidazole ring, it is obvious that substantially pure optical isomers of the desired imidazole-5-carboxylic acid esters of formula (I) may alternatively be obtained by resolving a racemic mixture of said esters with an appropriate strong optically active acid such as, for example, the dextro- and levo-forms of 10-camphorsulphonic acid, 3-bromo-camphor-9-sulphonic acid and the like, by the application of methodologies known to those skilled in the art.

Since one of the optically isomeric forms, more particularly the one having the S-(−) configuration, of the compounds of formula (I) is less preferred as a hypnotic agent, it would be economically advantageous if such S-(−) form of the compounds (I) as well as of the precursor carboxylic acid could be further utilized in the production of the desired dextrorotatory isomers R-(+) (I), for example, by first racemizing such S-(−) forms and then resolving the thus-obtained racemate as previously described. Such an objective is also fulfilled by the present invention.

It has thus been found that S-(−) 1-(1-phenylethyl)-1H-imidazole-5-carboxylic acid as well as S-(−)-loweralkyl 1-(1-phenylethyl)-1H-imidazole-5-carboxylate may be transformed into their respective racemic forms upon treatment with a catalytic amount of an appropriate strong base, preferably in an appropriate solvent. Suitable bases for this purpose include strong alkali metal bases, such as, for example, alkali metal hydrides, e.g., sodium hydride, and the like; alkali metal loweralkoxides, e.g. potassium t-butoxide, sodium methanolate, sodium ethanolate and the like; alkali metal amides, e.g., sodium amide and the like; and certain organometallic compounds such as, for example, butyl lithium and phenyl lithium. When the compound subjected to racemization is S-(−) 1-(1-phenylethyl)-1H-imidazole-5-carboxylic acid, it is preferably used in the form of a metal salt, in which case less of the basic catalyst is to be employed.

Suitable solvents for the racemization include polar organic solvents such as, for example, hexamethylphosphoric triamide, dimethyl formamide and dimethylsulfoxide. Somewhat elevated temperatures are appropriate to enhance the rate of racemization and preferably the reaction is carried out in an inert atmosphere at temperatures of from about 20° C to about 120° C. The reaction mixture is allowed to cool, then diluted with water, and the resultant aqueous phase is separated and acidified to about neutral pH to yield the racemic acid in crystalline form.

When the compound subjected to racemization is an isomer of 1-(1-phenylethyl)-1H-imidazole-5-carboxylic acid, the resultant racemate may be obtained from the reaction mixture by extraction with water. Acidification of the aqueous extract to about neutral pH yields the racemate in crystalline form. The racemic form which is obtained may in turn be resolved into its dextro- and levo-isomeric forms according to the procedure described herebefore.

When an isomeric form of a loweralkyl ester of formula (I) is racemized, the resultant racemate may be obtained from the reaction mixture by extraction with an inert organic non-polar solvent, for example, an aromatic hydrocarbon such as benzene, toluene, xylene and the like. The racemic ester which is obtained may be hydrolyzed to obtain the corresponding free acid which may subsequently be subjected to resolution.

Although emphasis is laid on the racemization of the less desired levo-isomers, the same procedure is applicable to the dextro-isomers when it is desirable to transform a dextro-isomer into a racemic mixture. Such a procedure is also intended to be within the scope of this invention.

The following examples are given in order to illustrate and not to limit the invention thereto. Unless otherwise stated all parts are by weight and the symbol $[\alpha]$ stands for $\alpha_D^{20}$.

EXAMPLE I

To a stirred mixture of 104.1 parts of (+)-2-[N-(1-phenylethyl)amino]acetonitrile and 1440 parts of dimethylbenzene are added dropwise 66 parts of formic acid (slightly exothermic reaction). Upon completion, stirring is continued for 3 hours at reflux temperature (water-separator). The reaction mixture is cooled to about 60° C. and washed successively with water, a sodium bicarbonate solution, a diluted sodium hydroxide solution and again twice with water. The organic phase is separated, dried, filtered and evaporated. The residue is crystallized from 2,2'-oxybispropane. The product is filtered off, washed with 2,2'-oxybispropane and dried, yielding (+)-N-(cyanomethyl)-N-(1-phenylethyl)-formamide (41%); m.p. 78.9° C.; $[\alpha]$ = +60.90° (1% CH$_3$OH).

To 200 parts of ethanol are added portionwise 12.5 parts of sodium. When all sodium is entered into solution, the ethanol is distilled off while meantime 900 parts of dimethylbenzene are added dropwise. Upon completion, the whole is allowed to cool to room temperature. Then there is added dropwise, at a temperature of about 15° C., a solution of 50 parts of (+)-N-(cyanomethyl)-N-1-phenylethyl)formamide in 80 parts of ethyl formamide, followed by the addition of 90 parts of dimethylbenzene. The mixture is stirred overnight (about 16 hours) at room temperature. 300 Parts of water are added and the whole is further stirred for 15 minutes. The layers are separated and the organic phase is extracted with water. 300 Parts of trichloromethane are added to the combined aqueous phases. The whole is heated to 50° C. and acidified with a hydrochloric acid solution. The layers are separated and the aqueous phase is extracted with trichloromethane. The combined organic phases are dried, filtered and evaporated, yielding (+)-N-(1-cyano-2-oxoethyl)-N-(1-phenylethyl)-formamide as a residue.

To a stirred mixture of 66 parts of (+)-N-(1-cyano-2-oxoethyl)-N-(1-phenylethyl)formamide, 36 parts of hydrochloric acid solution, 200 parts of water and 160 parts of ethanol is added dropwise a solution of 29 parts of potassium thiocyanate in 50 parts of water. Upon completion, stirring is continued for 3 hours at reflux temperature. While cooling to room temperature, the product is allowed to crystallize. It if filtered off, washed with a mixture of ethanol and water (1 : 1 by volume) and recrystallized from ethanol, yielding, after drying in air, (+)-2-mercapto-1-(1-phenylethyl)-1H-imidazole-5-carboxamide hydrate; m.p. 245.3° C.; $[\alpha]$ = +84.7°, (c = 1% CH$_3$OH).

To 80 parts of ethanol, previously saturated with gaseous ammonia, are added 2.3 parts of (+)-2-mercapto-1-(1-phenylethyl)-1H-imidazole-5-carboxamide hydrate and 6 parts of Raney-nickel. The mixture is stirred and refluxed for 2 hours and thereafter allowed to cool to room temperature. The Raney-nickel is filtered off and the filter-cake is washed with ethanol. The filtrate is evaporated in vacuo and the residue is purified by column-chromatography over silica gel using a mixture of trichloromethane and 5% of methanol as eluent. The pure fractions are collected and the eluent is evaporated, yielding (+)-1-(1-phenylethyl)-1H-imidazole-5-carboxamide, essentially free of its (−)-isomer, as a residue.

To a stirred and cooled (−10° C.) solution of 3.7 parts of (+)-1-(1-phenylethyl)-1H-imidazole-5-carboxamide in 50 parts of pyridine are added dropwise, during a 15 minute period, 3.4 parts of phosphoryl chloride. The mixture is allowed to reach room temperature; then heated in a boiling water-bath for 1.5 hrs. The reaction mixture is cooled to room temperature and poured onto 250 parts of ice-water. The precipitated product is filtered off, washed with water and dissolved in trichloromethane. The solution is dried, filtered and evaporated. The solid residue is crystallized from a mixture of 2,2'-oxybispropane and ethanol, yielding (+)-1-(1-phenylethyl)-1H-imidazole-5-carbonitrile; m.p. 129.3° C; $[\alpha]$ = +40.56° (c = 1% CH$_3$OH).

EXAMPLE II

A. To a stirred mixture of 110 parts of (−)-2-[N-(1-phenylethyl)amino]acetonitrile and 1500 parts of dimethylbenzene are added dropwise 70 parts of formic acid (slightly exothermic reaction). Upon completion, stirring is continued first for 3 hours at reflux temperature (water-separator) and further over week-end (about 63 hours) at room temperature. The reaction mixture is heated to 60° C and washed successively with water, a sodium bicarbonate solution, a diluted sodium hydroxide solution and again twice with water. The organic phase is separated, dried, filtered and evaporated. The residue is crystallized from a mixture of 80 parts of ethanol and 108 parts of 2,2′-oxybispropane. The product is filtered off and dried, yielding 46.5% of (−)-N-(cyanomethyl)-N-(1-phenylethyl)formamide; m.p. 78.8° C.; [α] = −60.7° (c = 1% CH$_3$OH).

To 200 parts of ethanol are added portionwise 16 parts of sodium. When all sodium is entered into solution, the ethanol is distilled off while meantime 1080 parts of dimethylbenzene are added dropwise. Upon completion, the whole is allowed to cool to room temperature. Then there is added dropwise, at a temperature of about 15° C., a solution of 60 parts of (−)-N-(cyanomethyl)-N-(1-phenylethyl)formamide in 96 parts of ethyl formate, followed by the addition of 90 parts of dimethylbenzene. The mixture is stirred overnight at room temperature. 300 Parts of water are added and the whole is further stirred for 15 minutes. The layers are separated and the organic phase is extracted with water. 300 Parts of trichloromethane are added to the combined aqueous phases. The whole is heated to 50° C. and acidified with a hydrochloric acid solution. The layers are separated and the aqueous phase is extracted with trichloromethane. The combined organic phases are dried, filtered and evaporated, yielding (−)-N-(1-cyano-2-oxoethyl)-N-(1-phenylethyl)formamide as a residue.

To a stirred mixture of 66 parts of (−)-N-(1-cyano-2-oxoethyl)-N-(1-phenylethyl)formamide, 36 parts of hydrochloric acid solution, 200 parts of water and 160 parts of ethanol is added dropwise a solution of 29 parts of potassium thiocyanate in 50 parts of water. Upon completion, stirring is continued for 3 hours at reflux temperature. While cooling to room temperature, the product is allowed to crystallize. It is filtered off, washed with a mixture of ethanol and water (1 : 1 by volume) and recrystallized from ethanol, yielding, after drying at the air, (−)-2-mercapto-1-(2-phenylethyl)-1H-imidazole-5-carboxamide hydrate; m.p. 244.8° C.; [α] = −85.8° (c = 1% CH$_3$OH).

To 80 parts of ethanol, previously saturated with gaseous ammonia, are added 2.3 parts of (−)-2-mercapto-1-(2-phenylethyl)-1H-imidazole-5-carboxamide hydrate and 6 parts of Raney-nickel. The mixture is stirred and refluxed for 2 hours and thereafter allowed to cool to room temperature. The Raney-nickel is filtered off and the filter-cake is washed with ethanol. The filtrate is evaporated in vacuo and the residue is purified by column-chromatography over silica gel using a mixture of trichloromethane and 5% of methanol and eluent. The pure fractions are collected and the eluent is evaporated, yielding (−)-1-(1-phenylethyl)-1H-imidazole-5-carboxamide, essentially free of its (+)-isomer, as a residue.

B. To a stirred and cooled (−10° C.) solution of 3.7 parts of (−)-1-(1-phenylethyl)-1H-imidazole-5-carboxamide in 50 parts of pyridine are added dropwise, during a 15 minute period, 3.4 parts of phosphoryl chloride. The mixture is allowed to reach room temperature; then heated in a boiling water-bath for 1.5 hrs. The reaction mixture is cooled to room temperature and poured onto 250 parts of ice-water. The precipitated product is filtered off, washed with water and dissolved in trichloromethane. The solution is dried, filtered and evaporated. The solid residue is crystallized from a mixture of 2,2′-oxybispropane and ethanol, yielding (−)-1-(1-phenylethyl)-1H-imidazole-5-carbonitrile; m.p. 128.7° C.; [α] = +40.23° (c = 1% CH$_3$OH).

By repeating the procedure of Example II-A and using an equivalent amount of (±)-2-[N-(1-phenylethyl)amino]acetonitrile as a starting material there is obtained (±)-1-(1-phenylethyl)-1H-imidazole-5-carboxamide; m.p. 136.5°–137° C.

By repeating the procedure of Example II-B and using an equivalent amount of (±)-1-(1-phenylethyl)-1H-imidazole-5-carboxamide in place of the (−)-isomer used therein, there is obtained (±)-1-(1-phenylethyl)-1H-imidazole-5-carbonitrile; m.p. 97°–99° C.

EXAMPLE III

A. To a stirred mixture of 40 parts of ethanol and 3 parts of (+)-1-(1-phenylethyl)-1H-imidazole-5-carboxamide there are added slowly 10 parts of concentrated sulfuric acid. Upon completion, stirring at reflux is continued for 7 hours. After this period, the mixture is allowed to cool to room temperature and poured onto crushed ice. The ethanol is distilled off, and the aqueous phase is alkalized with sodium hydroxide and extracted three times with trichloromethane. The combined extracts are dried, filtered and evaporated. The residue is converted into the sulfate salt in 2-propanol and 2,2′-oxybispropane. The salt is filtered off, washed with 2,2′-oxybispropane and dried, yielding R-(+)-ethyl 1-(α-methylbenzyl)-5-imidazolecarboxylate sulfate; m.p. 111° C.; [α]$_D^{20}$ = +22.1° (c = 1% CH$_3$OH).

B. The foregoing procedure was repeated, except that the (+)-1-(1-phenylethyl)-1H-imidazle-5-carboxamide used therein was replaced by an equivalent amount of (−)-1-(1-phenylethyl)-1H-imidazole-5-carboxamide and there was obtained (−)-ethyl 1-(1-phenylethyl)-1H-imidazole-5-carboxylate sulfate; [α] = −22.5° (c = 1% CH$_3$OH).

EXAMPLE IV

A. Gaseous hydrogen chloride is introduced through 40 parts of ethanol till saturation while cooling at 0° C. Then there are added 2.5 parts of (+)-1-(1-phenylethyl)-1H-imidazole-5-carbonitrile and the whole is stirred and refluxed for 24 hours. The reaction mixture is poured onto water. The whole is alkalized with sodium hydroxide and extracted three times with trichloromethane. The combined extracts are dried, filtered and evaporated. The residue is converted into the sulfate salt in 2-propanol and 2,2′-oxybispropane. The precipitated sulfate salt is filtered off, washed with 2,2′-oxybispropane and dried, yielding R-(+)-ethyl 1-(α-methylbenzyl)-5-imidazolecarboxylate sulfate; mp. 111.7° C.; ]α]$_D^{20}$ = +22.4° (c = 1% CH$_3$OH).

B. The foregoing procedures was repeated, except that the (+)-1-(1-phenylethyl)-1H-imidazole-5-carbonitrile used therein is replaced by an equivalent amount of (−)-1-(1-phenylethyl)-1H-imidazole-5-carbonitrile, yielding (−)-ethyl 1-(1-phenylethyl)-1H-imidazole-5-carboxylate sulfate; [α] = −22.3° (c = 1% CH$_3$OH).

EXAMPLE V

To a stirred and refluxing mixture of 13 parts of (±)-1-(1-phenylethyl)-5-imidazolecarboxylic acid and 200 parts of 2-propanol are added 3.6 parts of (−)-α- methylbenzenemethanamine and the whole is stirred and refluxed for 10 minutes. The reaction mixture is allowed to cool to room temperature. The precipitated product is filtered off (the filtrate is set aside), washed with 2-propanol and crystallized from 160 parts of 2-propanol. It is filtered off and dried over week-end in vacuo at 60° C., yielding (−)-1-(1-phenylethyl)-1H-imidazole-5-carboxylic acid salt with (−)-α-methylbenzenemethanamine; m.p. 194° C.; $[\alpha]_D = -51.0°$ (c = 1% in water).

To the filtrate (see above) are added 3.6 parts of (+)-α-methylbenzenemethanamine and the whole is stirred and refluxed for 10 minutes. The reaction is allowed to cool to room temperature. The precipitated product is filtered off, washed with 2-propanol and dried in vacuo for 4 hours at 60° C., yielding (+)-1-(1-phenylethyl)-1H-imidazole-5-carboxylic acid salt with (+)-α-methylbenzenemethanamine; m.p. 190.3° C.; $[\alpha]_D$ +52.9° (c = 1% in water).

EXAMPLE VI

A stirring mixture of 2.55 parts of (+)-α-methylbenzylamine salt with R-(+)-1-(α-methylbenzyl)-5-imidazolecarboxylic acid and 24 parts of dry absolute ethanol is saturated with gaseous hydrogen chloride. Upon completion, stirring is continued for 7 hours at reflux temperature, while gaseous hydrogen chloride is still introduced. The reaction mixture is evaporated and the residue is taken up in 30 parts of water. The resulting solution is adjusted to pH = 6 with a sodium hydroxide solution 1 0N and the product is extracted three times with trichloromethane. The combined extracts are dried, filtered and evaporated. The residue is taken up in 2.4 parts of 2-propanol and the solution is filtered. The filtrate is acidified with sulfuric acid and warmed for a while. 2,2′-Oxybispropane is added till almost turbid and upon scratching, the product is precipitated while cooling in an ice-bath. It is filtered off, washed with a mixture of 2-propanol and 2,2′-oxybispropane, and dried, yielding 80% of R-(+)ethyl 1-(α-methylbenzyl)-5-imidazolecarboxylate sulfate; $[\alpha]$ = +22.5° (c = 0.1% H₂O).

EXAMPLE VII

A stirring mixture of 2.55 parts of S-(−)-1-(1-phenylethyl)1H-imidazole-5-carboxylic acid salt with (−)-α-methylbenzenemethanamine and 24 parts of dry absolute ethanol is saturated with gaseous hydrogen chloride. Upon completion, stirring is continued for 7 hours at reflux temperature, while gaseous hydrogen chloride is still introduced. The reaction mixture is evaporated and the residue is taken up in 30 parts of water. The solution is adjusted to pH = 6 with a sodium hydroxide solution 10N and the product is extracted three times with trichloromethane. The combined extracts are dried, filtered and evaporated. The residue is converted into the nitrate salt in methylbenzene while cooling in an ice-bath. The salt is filtered off, washed with methylbenzene and dried, yielding 52% of S-(−)-ethyl 1(α-methylbenzyl)imidazole-5-carboxylate nitrate; $[\alpha]$ = −31.9° (c = 0.1% H₂O).

EXAMPLE VIII

A. A mixture of 1 part of (+)-α-methylbenzylamine salt with R-(+)-1-(α-methylbenzyl)-5-imidazolecarboxylic acid and 6 parts of sodium hydroxide solution 1N is shaken in a closed tube till all solid enters solution (pH = ±11). The resulting solution is shaken five times for 1 minute, each time after the addition of 1.4 parts of 2,2′-oxybispropane. The organic phases are combined (the alkaline aqueous phase is set aside) and evaporated, yielding R-(+)-α-methylbenzylamine.

The alkaline aqueous phase (see above) is adjusted to pH = 6.2 with acetic acid. While cooling in ice-water and upon scratching, the product is precipitated. It is filtered off and crystallized twice from 2-propanol, yielding, after drying for 3 hours in vacuo at 60° C., R-(+)-1-(α-methylbenzyl)-5-imidazolecarboxylic acid; m.p. 155° C.; $[\alpha]$ = +65.9° (c = 1% H₂O).

B. By repeating the foregoing procedure, except that an equivalent amount of (−)-1-(1-phenylethyl)-1H-imidazole-5-carboxylic acid salt with (−)-α-methylbenzenemethanamine is used, there is obtained (−)-1-(1-phenylethyl)-1H-imidazole-5-carboxylic acid; m.p. 155.2° C.; $[\alpha]_D = -67.8°$ (c = 0.1% H₂O).

EXAMPLE IX

A. A mixture of 10 parts of R-(+) 1-(α-methylbenzyl)-5-imidazolecarboxylic acid and 105 parts of sulfinyl chloride is stirred and refluxed for 2 hours. The reaction mixture is cooled and diluted with 2,2′-oxybispropane. The precipitated product is filtered off, washed with 2,2′-oxybispropane and dried, yielding 90% of (+)-1-(1-phenylethyl)-1H-imidazole-5-carbonyl chloride hydrochloride.

B. A mixture of 25.5 parts of (−)-1-(1-phenylethyl)-1H-imidazole-5-carboxylic acid and 280 parts of sulfinyl chloride is stirred and refluxed for 2 hours. The reaction mixture is cooled in an ice-bath. The product crystallizes upon the addition of 2,2′-oxybispropane. It is filtered off, washed with 2,2′-oxybispropane and dried, yielding 94% of (−)-1-(1-phenylethyl)-1H-imidazole-5-carbonyl chloride hydrochloride.

EXAMPLE X

A mixture of 5.5 parts of (+)-1-(1-phenylethyl)-1H-imidazole-5-carbonyl chloride hydrochloride and 80 parts of methanol is stirred and refluxed overnight. The reaction mixture is cooled and evaporated. The residue is dissolved in 100 parts of water, alkalized with sodium hydroxide and the product is extracted with 2,2′-oxybispropane. The extract is dried, filtered and evaporated. The residue is converted into the sulfate salt in 2-propanol and 2,2′-oxybispropane. The salt is filtered off, washed with 2,2′-oxybispropane and dried, yielding 73% of (+)-methyl 1-(1-phenylethyl)-1H-imidazole-5-carboxylate sulfate; m.p. 103.8° C.; $[\alpha]$ = +20.51° (c = 1% CH₃OH).

EXAMPLE XI

A mixture of 5.5 parts of (+)-1-(1-phenylethyl)-1H-imidazole-5-carbonyl chloride hydrochloride and 80 parts of 1-propanol is stirred and refluxed overnight. The reaction mixture is cooled and evaporated. The residue is dissolved in 100 parts of water and the solution is alkalized with a sodium hydroxide solution. The product is extracted with 2,2′-oxybispropane. The extract is dried, filtered and evaporated. The residue is converted into the sulfate salt in 2-propanol and 2,2′-oxybispropane. The salt is filtered off, washed with 2,2′-oxybispropane and dried, yielding 65% of (+)-propyl 1-(1-phenylethyl)-1H-imidazole-5-carboxylate sulfate hydrate; m.p. 106° C.; $[\alpha]$ = +22.68° (c = 1% CH₃OH).

EXAMPLE XII

A mixture of 5.5 parts of (−) -1-(1-phenylethyl)-1H-imidazole-5-carbonyl chloride hydrochloride and 80 parts of methanol is stirred and refluxed overnight. The reaction mixture is cooled and evaporated. The residue is dissolved in water and the alkalized is akalized with a sodium hydroxide solution 60%. The product is extracted with 2,2′-oxybispropane. The extract is dried, filtered and evaporated. The residue is converted into the sulfate salt in 2-propanol and 2,2′-oxybispropane. The salt is filtered off and dried, yielding 60% of (−)-methyl 1-(1-phenylethyl)-1H-imidazole-5-carboxylate sulfate; m.p. 97.8° C.; [α] = −22.39° (c = 1% CH$_2$OH).

EXAMPLE XIII

A mixture of 5.5 parts of (−)-1-(1-phenylethyl)-1H-imidazole-5-carbonyl chloride hydrochloride and 80 parts of 1-propanol is stirred and refluxed overnight. The reaction mixture is cooled and evaporated. The residue is dissolved in water. The solution is alkalized with a sodium hydroxide solution 60%. The product is extracted with 2,2′-oxybispropane. The extract is dried, filtered and evaporated. The residue is converted into the sulfate salt in 2-propanol and 2,2′-oxybispropane. The salt is filtered off and dried, yielding 60% of (−)-propyl 1-(1-phenylethyl)-1H-imidazole-5-carboxylate sulfate hydrate; m.p. 73.3° C.; [α] = −22.24° (c = 1% CH$_3$OH).

EXAMPLE XIV

A solution of 47.5 parts of (−)-ethyl 1-(1-phenylethyl)-1H-imidazole-5-carboxylate sulfate in 500 parts of water is alkalized with 14 parts of a sodium hydroxide solution 50%. The product is extracted twice with 325 parts of dichloromethane. The combined extracts are dried, filtered and evaporated in vacuo. The residue is crystallized from 2,2′-oxybispropane, yielding (−)-ethyl 1-(1-phenylethyl)-1H-imidazole-5-carboxylate.

A mixture of 12.21 parts of (−)-ethyl 1-(1-phenylethyl)-1H-imidazole-5-carboxylate, 1.9 parts of a 61.8% suspension of sodium hydride in mineral oil and 50 parts of hexamethylphosphoric triamide is heated to 100° C. while Argon-gas is introduced, and further stirred at this temperature for 20 hours. The mixture is allowed to cool to room temperature and there are added 110 parts of benzene. The whole is washed three times with water. The organic phase is dried, filtered and evaporated. The residue is converted into the hydrochloride salt in 2-propanol. The crude salt is filtered off and crystallized from 2,2′-oxybispropane, yielding (±)-ethyl 1-(1-phenyethyl)-1H-imidazole-5-carboxylate hydrochloride; m.p. 139.5° C.

EXAMPLE XV

A mixture of 17.7 parts of (−)-1-(1-phenylethyl)-1H-imidazole-5-carboxylic acid, 3.28 parts of sodium hydroxide and 120 parts of 2-propanol is stirred and refluxed until the reaction mixture becomes homogeneous and thereafter for 1 further hour. During reflux part of the product crystallizes out. The reaction mixture is allowed to cool to room temperature and the precipitated product is filtered off. The product is washed with 2-propanol and dried in vacuo, yielding (−)-1-(1-phenylethyl)-1H-imidazole-5-carboxylic acid sodium salt.

A mixture of 14.3 parts of (−)-1-(1-phenylethyl)-1H-imidazole-5-carboxylic acid sodium salt, 1.9 parts of a 61.8% suspension of sodium hydride in mineral oil and 60 parts of hexamethylphosphoric triamide is stirred for 20 hours at 100° C. under Argon atmosphere. The mixture is allowed to cool at room temperature and poured onto 150 parts of water. The whole is washed three times with 200 parts of dichloromethane. The aqueous phase is neutralized (pH 7) with acetic acid and the product is allowed to crystallize. The product is filtered off, dried and recrystallized from ethanol, yielding (±)-1-(1-phenylethyl)-1H-imidazole-5-carboxylic acid; m.p. 188° C.

EXAMPLE XVI

40 Parts of R-(+)-ethyl 1-(α-methylbenzyl)imidazole-5-carboxylate nitrate are dissolved in water and the solution is alkalized with sodium carbonate. After extraction with chloroform, the latter is dried and evaporated. The residue is dissolved in diisopropylether and the solution is acidified with gaseous hydrogen chloride: an oil is precipitated. It is dissolved in water, alkalized with ammonium hydroxide and the free base is extracted with chloroform. The extract is dried and evaporated. To the residue are added a few parts of diisopropylether and the whole is seeded with a crystal of dl-ethyl 1-(α-methylbenzyl)imidazole-5-carboxylate. After cooling for 4 hours at −20° C., the precipitated product is filtered off and dried, yielding 20 parts of R-(+)-ethyl 1-(α-methylbenzyl)imidazole-5-carboxylate; m.p. 67° C.; $α_D^{20}$ : +66° (c = 1% ethanol).

What is claimed is:

1. A method of preparing racemic 1-(1-phenylethyl)-1H-imidazole-5-carboxylic acid which comprises treating a member selected from the group consisting of the (+)-isomer and (−)-isomer of said acid with a strong base in a polar organic solvent at from about 20° to about 120° C.

2. A method of preparing racemic 1-(1-phenylethyl)-1H-imidazole-5-carboxylic acid which comprises treating an alkali metal salt of a member selected from the group consisting of the (+)-isomer and (−)-isomer of said acid with sodium hydride in hexamethylphosphoric triamide at from about 20° to about 120° C in an inert gas atmosphere, diluting the cooled reaction mixture with water and acidifying the resultant aqueous phase to about neutral pH to yield crystallized racemic 1-(1-phenylethyl)-1H-imidazole-5-carboxylic acid.

3. A method of preparing racemic loweralkyl 1-(1-phenylethyl)-1H-imidazole-5-carboxylate which comprises treating a member selected from the group consisting of the (+)-isomer and (−)-isomer of said ester with a strong base in a polar organic solvent at from about 20° to about 120° C.

4. A method of preparing racemic ethyl 1-(1-phenylethyl)-1H-imidazole-5-carboxylate which comprises treating a member selected from the group consisting of the (+)-isomer and (−)-isomer of said ester with sodium hydride in hexamethylphosphoric triamide at from about 20° to about 120° C in an inert gas atmosphere and extracting the racemic ethyl 1-(1-phenylethyl)-1H-imidazole-5-carboxylate from the reaction mixture with an inert non-polar organic solvent.

* * * * *

UNITED STATES PATENT AND TRADEMARK OFFICE
CERTIFICATE OF CORRECTION

PATENT NO. : 3,991,072
DATED : November 9, 1976
INVENTOR(S) : Roevens et al.

It is certified that error appears in the above-identified patent and that said Letters Patent are hereby corrected as shown below:

```
In Column  6, line 15, mutatis mutandis should be underscored
In Column  8, line  9, "formamide" should read ---formate---
In Column  8, line 29, "if" should read ---is---
In Column 10, line  5, "+" should read "-"
In Column 10, line 35, "imidazle" should read ---imidazole---
In Column 10, line 51, "]" should read ---[---
In Column 11, line 13, "The reaction is" should read ---
---The reaction mixture is ---

In Column 13, line  8, "alkalized" should read ---solution---
In Column 13, line 16, "CH2" should read ---CH3---
In Column 14, line 24, "precipited" should read ---precipitated---
```

Signed and Sealed this

Eighteenth Day of April 1978

[SEAL]

Attest:

RUTH C. MASON
Attesting Officer

LUTRELLE F. PARKER
Acting Commissioner of Patents and Trademarks